US007485166B2

(12) United States Patent
Safuto

(10) Patent No.: US 7,485,166 B2
(45) Date of Patent: Feb. 3, 2009

(54) DEVICE AND METHOD FOR DETECTION, COLLECTION, CONTAINMENT, NEUTRALIZATION, AND ELIMINATION OF TOXIC OR OTHER CONTAMINANT AEROSOLS

(76) Inventor: Joseph Safuto, P.O. Box 4211, Glendale, CA (US) 91222

( * ) Notice: Subject to any disclaimer, the term of this patent is extended or adjusted under 35 U.S.C. 154(b) by 588 days.

(21) Appl. No.: 11/106,885

(22) Filed: Apr. 15, 2005

(65) Prior Publication Data

US 2006/0162301 A1     Jul. 27, 2006

Related U.S. Application Data

(60) Provisional application No. 60/563,203, filed on Apr. 17, 2004.

(51) Int. Cl.
| | |
|---|---|
| B01D 50/00 | (2006.01) |
| B01D 46/00 | (2006.01) |
| E03D 1/00 | (2006.01) |
| E03D 13/00 | (2006.01) |
| E03D 1/36 | (2006.01) |
| E03D 1/06 | (2006.01) |
| E03D 9/04 | (2006.01) |
| A47K 13/00 | (2006.01) |
| E03F 5/08 | (2006.01) |
| B65D 6/40 | (2006.01) |
| B65D 55/00 | (2006.01) |
| B65D 41/56 | (2006.01) |
| B65D 25/28 | (2006.01) |
| B65D 51/16 | (2006.01) |

(52) U.S. Cl. .................. 55/385.1; 95/273; 4/300; 4/301; 4/234; 4/235; 4/367; 4/371; 4/222; 4/213; 4/214; 4/215; 4/216; 4/217; 220/200; 220/371; 220/203.22; 220/212; 220/212.5

(58) Field of Classification Search ............... 55/385.1, 55/385.4; 95/273; 4/300, 301, 234, 235, 4/367.1, 371, 222, 213–217; 220/200, 371, 220/203.22, 212, 212.5
See application file for complete search history.

(56) References Cited

U.S. PATENT DOCUMENTS 2,849,727 A   9/1958   Bollinger et al.

(Continued)

OTHER PUBLICATIONS

U.S. Environmental Protection Agency, Indoor Air- Publications, "Biological Pollutants in Your Home," by Consumer Product Safety Commission (CPSC) and the American Lung Association, The Christmas Seal People; IAQ Publications, www.epa.gov.

(Continued)

Primary Examiner—Walter D Griffin
Assistant Examiner—Amber Miller Harris
(74) Attorney, Agent, or Firm—Peter Ganjian

(57) ABSTRACT

The present invention provides a device for detection, collection, containment, neutralization, and elimination of aerosolized contaminants, comprising a lid that fully covers an edge of a container for containment of exiting aerosolized contaminants, with the lid having housing for accommodating an article. The housing comprising a top vent aligned along atop of a bottom vent, with the top vent optionally smaller in size than the bottom vent, and with the housing, the top vent, and the bottom vent located normal to a natural vertical upward move of the aerosolized contaminants. The aerosolized contaminants are detected, collected, contained, neutralized, and eliminated and sanitized by the article within the housing, allowing only uncontaminated air out of the top vent through a natural upward movement of the aerosolized contaminants via the force of the flush.

19 Claims, 14 Drawing Sheets

U.S. PATENT DOCUMENTS

| | | | | |
|---|---|---|---|---|
| 3,365,063 | A * | 1/1968 | Cobb et al. | 210/167.01 |
| 3,579,663 | A * | 5/1971 | Ware et al. | 4/230 |
| 3,689,944 | A | 9/1972 | Clayton | 4/213 |
| 4,301,555 | A | 11/1981 | Poister | 4/217 |
| 4,344,194 | A | 8/1982 | Pearson | 4/213 |
| 4,586,201 | A | 5/1986 | Todd, Jr. | 4/217 |
| 4,843,656 | A * | 7/1989 | Forman | 4/237 |
| 5,079,783 | A | 1/1992 | Haletsky et al. | 4/217 |
| 5,426,793 | A | 6/1995 | Mac | 4/237 |
| 5,429,240 | A * | 7/1995 | Biebel et al. | 206/455 |
| 5,539,937 | A | 7/1996 | Barefoot | 4/213 |
| 5,864,892 | A | 2/1999 | Cool | 4/222 |
| 6,226,807 | B1 * | 5/2001 | Rozenblatt et al. | 4/431 |
| 6,546,567 | B2 | 4/2003 | Kuzniar | |
| 6,895,604 | B1 * | 5/2005 | Ramsey | 4/213 |
| 2004/0019960 | A1 | 2/2004 | Kuzniar | |

OTHER PUBLICATIONS

The CLE@NZINE Your Industry News—First, Do your toilets make you sick? The sneeze effect, SneezeEffect.html; www.thecleanzine.com/pages/sneezeeffect,html.

Panasonic, "Matsushita (Panasonic) Develops New Air Filter Capable of Inactivating Various Allergens and SARS Virus," Jul. 9, 2004, 2004, http://www.panasonic.co.jp/global/top.html.

Applied Microbiology (American Society of Microbiology), vol. 30, No. 2, Aug. 1975, p. 229-237, titled "Microbiological Hazards of Household Toilets: Droplet Production and the Fate of Residual Organisms," by Charles P. Gerba et.

Consensus Statement by the World Health Organization (WHO) in Rome, Sep. 23-25, 2003, Titled "WHO Informal Consultation On The Transmission Of SARS CoV And Other Pathogenic Viruses Through Fecal Droplets."

The New England Journal of Medicine, published Apr. 22, 2004, vol. 350:1731-1739, No. 17, titled "Evidence of Airborne Transmission of the Severe Acute Respiratory Syndrome Virus."

* cited by examiner

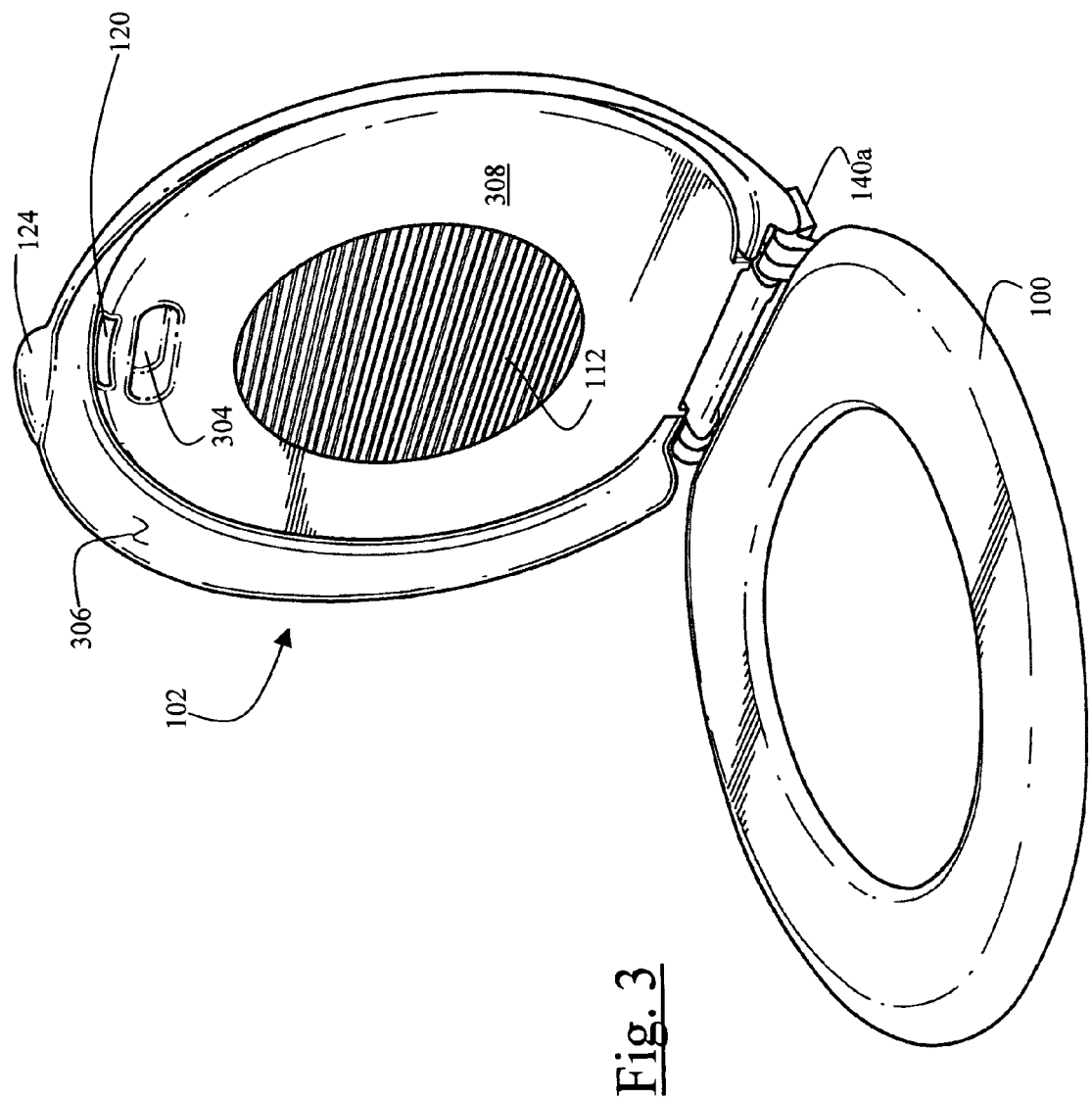

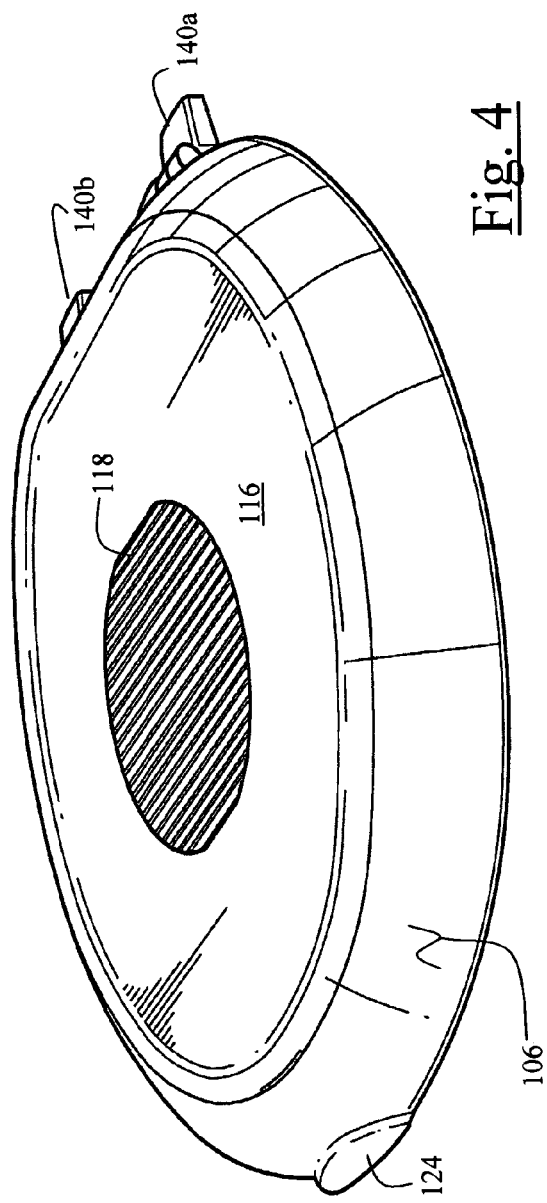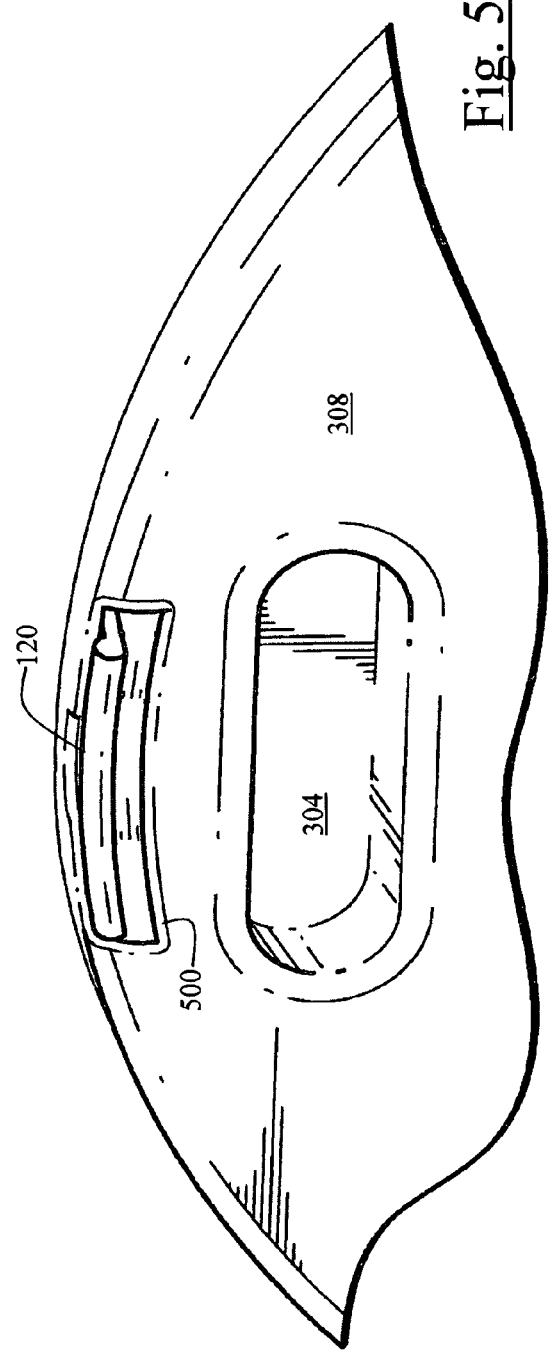

DEVICE AND METHOD FOR DETECTION, COLLECTION, CONTAINMENT, NEUTRALIZATION, AND ELIMINATION OF TOXIC OR OTHER CONTAMINANT AEROSOLS

CROSS-REFERENCE TO RELATED APPLICATIONS

The present application claims priority from related U.S. Provisional Application Ser. No. U.S. 60/563,203, filed Apr. 17, 2004, the entire disclosure of which is incorporated herein by reference.

BACKGROUND OF THE INVENTION (1) Field of the Invention

This invention relates in general to lids and pertains, more particularly, to toilet lids for detection, collection, containment, neutralization, and elimination of aerosolized contaminants such as fecal and urinary matter, and various airborne toxic, virus and bacterial mist.

(2) Description of Related Art

Based on extensive research, it has been proven that after each toilet flush an airborne bacterial and viral plume permeates the entire bathroom or water closet area leaving a residue on anything within the "flush zone." Whether the toilet lid is closed or open, after every flush fecal, urine, and toxic aerosol (droplets in mist form) can spew up to about 20 feet away (also known as the "sneeze effect"), landing on any item within range.

A study published in Applied Microbiology (American Society of Microbiology), Vol. 30, No. 2, August 1975, p. 229-237, titled "Microbiological Hazards of Household Toilets: Droplet Production and the Fate of Residual Organisms," by Charles P. Gerba et al. disclosed the extensive transmission of viral aerosols from toilets. The study conducted in 1975 found that "bacteria and viruses in household toilets were shown to remain in the bowl after flushing, and even continual flushing could not remove a persistent fraction. The study further stated that "The detection of bacteria and viruses falling out onto surfaces in bathrooms after flushing indicated that they remain airborne long enough to settle on surfaces throughout the bathroom." The Gerba et al. study stated that "Thus there is a possibility that a person may acquire an infection from an aerosol produced by a toilet."

The Consensus Statement by the World Health Organization (WHO) in Rome, Sep. 23-25, 2003, Titled "WHO Informal Consultation On The Transmission Of SARS CoV And Other Pathogenic Viruses Through Fecal Droplets," hereinafter "WHO," discussed the "risks of transmission of SARS CoV amongst human population associated with the design and operation of sanitation facilities for the management of human excreta." More recently, concerning the WHO findings, The New England Journal of Medicine, published Apr. 22, 2004, Volume 350:1731-1739, Number 17, titled "Evidence of Airborne Transmission of the Severe Acute Respiratory Syndrome Virus," (or SARS) suggested a clear connection between the SARS virus and aerosolized fecal matter airborne through the simple act of flushing a toilet.

A plethora of conventional toilet lid devices integral with electromechanical air deodorizing devices for deodorizing the air from a toilet bowl are disclosed in the prior art. Reference is made to U.S. Pat. Nos. 5,539,937; 5,426,793; 5,079,783; 4,586,20; 4,344,194; 4,301,555; 3,689,944; and 2,849,727. Most use complicated electro-mechanical venting systems that include the use of electrical exhaust fans and air duct connected with the fans to electro-mechanically vent and remove odors from the toilet bowls, with others claiming the removal (or vacuuming) of odors and germs. Regrettably, according to WHO, it has been found that the use of mechanical devices as a venting system may exacerbate the spread of toxins, viruses, and bacteria rather than eliminate them. In fact, the recommendation of WHO was that "Whenever possible, venting systems should be free of mechanical devices." One reason for this is that air conduits or pipes, fans, etc. that are used in the prior art devices can easily become clogged with fecal, urine, and mildew, which can increase the spread of bacteria and viruses. In addition, most prior art devices disclosed require expensive structural modifications to the bathroom and the toilet seat and lid (addition of holes in the walls of the water closets to run the air pipes, place fans, etc.). They also require power to operate, which requires additional outlets or storage areas for batteries, requiring further structural modifications of the bathrooms, water closets, and toilets. Furthermore, all the additional mechanical features also require constant maintenance, which is an added cost to consumers.

The U.S. Pat. No. 5,864,892 to Cool disclosed a device and method for collecting and sanitizing toilet spray without the use of mechanical devices by placing a cover over a conventional toilet, including the toilet lid, seat, and bowl. However, with the Cool device, any liquid that drips along the exterior of the toilet bowl or on the underside of the toilet seat and does not contact the cover is not sanitized, and remains a potential agent for transmission of bacteria and viruses. Therefore, when the cover is removed for maintenance, the fecal and urinary residue in contact with the toilet bowl or seat can contaminate the person cleaning it, and cause the bacteria and viruses to become airborne again. In addition, the cover is not esthetically pleasing and alters the conventional manner in which toilets are generally used.

To date, no provision is made to ensure that the water splash and mist created during toilet flushing is collected, contained, neutralized, and eliminated within the toilet bowl. No prior art has provided a toilet lid for collection and containment of aerosolized toxic contaminants or fecal and urinary matter, including various airborne viruses and bacterial mist without the use of mechanical devices, modification of the toilet bowl or water closet, or addition of accessories such as toilet covers.

In light of the current state of the art and the drawbacks to current devices and methods mentioned above, a need exists for a toilet lid that would permit for detection, collection, containment, neutralization, and elimination of aerosolized contaminates such as toxins, or fecal and urinary matter including various airborne viruses and bacterial mist within the toilet bowl, without the use of mechanical venting systems, accessory covers, and modification of the toilet bowl or the water closet.

BRIEF SUMMARY OF THE INVENTION

The present invention provides a non-mechanical toilet seat and lid combination for detection, collection, containment, neutralization, and elimination of aerosolized contaminants, fecal and urinary matter, and various airborne toxins, viral, and bacterial mist, and works with the natural fluid dynamics caused by flushing a toilet that generates the vertical ascension of aerosols via the force of the flush.

One aspect of the present invention provides a device for collection, containment, neutralization, and elimination of aerosolized contaminants, comprising:

a lid that fully covers an edge of a container for containment of exiting aerosolized contaminants;

the lid having housing for accommodating an article;

the housing comprising a top vent aligned along atop of a bottom vent;

the housing, the top vent, and the bottom vent located normal to a natural vertical upward move of the aerosolized contaminants;

whereby aerosolized contaminants are detected, collected, contained, neutralized, and eliminated by the article within the housing, allowing only uncontaminated air out of the top vent through a natural upward movement of the aerosolized contaminants.

Another optional aspect of the present invention provides a device wherein the lid is further comprised of a shroud section that fully covers and extends past a bottom edge of the container for covering gaps between the lid and the container for containment of exiting aerosolized contaminants.

Another optional aspect of the present invention provides a device, including a lid cap having one of the top vent and the bottom vent.

Yet another optional aspect of the present invention provides a device wherein the housing further comprises:

an elongated recessed section at a distal end of the housing for accommodating a protruded tab located at a distal end of the lid cap; and an opening at a proximal end of the housing for accommodating a locking clip located at a proximal end of the lid cap;

whereby the protruded tab of the lid cap is inserted within the elongated recess of the housing, and the locking clip of the lid cap is snapped into the opening of the housing for securing the lid cap onto the housing.

Yet another optional aspect of the present invention provides a device wherein the housing further comprises:

an elongated recessed section at a distal end of the housing for accommodating a protruded tab located at a distal end of the lid cap; and an opening at a proximal end of the lid cap for accommodating a locking clip located at a proximal end of the housing;

whereby the protruded tab of the lid cap is inserted within the elongated recess of the housing, and the locking clip of the housing is snapped into the opening of the lid cap for securing the lid cap onto the housing.

A further optional aspect of the present invention provides a device wherein the lid cap further includes a right arch and a left arch located at a proximal end of the lid cap, proximal to either side of the locking clip for facilitating the removal and insertion of the lid cap from the housing.

Yet a further optional aspect of the present invention provides a device wherein the lid cap further includes a right arch and a left arch located at a proximal end of the lid cap, proximal to either side of the opening for facilitating the removal and insertion of the lid cap from the housing.

Another optional aspect of the present invention provides a device wherein the circumference edges of the lid cap fully inserts into the housing.

Yet another optional aspect of the present invention provides a device wherein the housing includes structure for securing the article therein, and for providing structural integrity and strength for the lid.

A further optional aspect of the present invention provides a device wherein the proximal end of an upper shroud section includes a lid lift tab for opening and closing of the lid.

Still a further optional aspect of the present invention provides a device wherein a proximal end of an underside of the lid, adjacent to the opening is comprised of a cavity for insertion of fingers for grasping the underside of the lid for removal of the locking clip from the opening.

Another optional aspect of the present invention provides a device wherein a proximal end of a top side of the lid cap, adjacent to the opening is comprised of a cavity for insertion of fingers for grasping the lid cap for removal of the locking clip from the opening.

A further optional aspect of the present invention provides a device wherein the locking clip is comprised of a cut-section of the circumference edge of the lid cap, suspended in a cantilever manner, with an elongated free side having a protrusion that locks within the opening of the lid.

Still a further optional aspect of the present invention provides a device wherein the locking clip is projected out and is integral with an underside of the lid, with an elongated free side having a protrusion that locks within the opening of the lid cap.

Another optional aspect of the present invention provides a device wherein the article includes a handle that allows for insertion and removal in a sliding manner within the housing.

A further optional aspect of the present invention provides a device wherein the article is replaceable.

Still a further optional aspect of the present invention provides a device wherein the lid is a toilet lid and the container is a toilet bowl.

Yet a further optional aspect of the present invention provides a device wherein the toilet lid is further connected to a toilet seat, with the toilet lid and the toilet seat coupled to the toilet bowl.

Another optional aspect of the present invention provides a device wherein the toilet seat is further comprised of a continuous seal coupled to an underside of the toilet seat for enclosing a second gap between the toilet seat and a top surface circumference edge of a toilet bowl for containment of exiting aerosolized contaminants.

Yet another optional aspect of the present invention provides a device wherein the top vent is smaller than the bottom vent.

A further optional aspect of the present invention provides a device wherein the lid cap couples to a main lid section for forming the lid.

These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention.

Referring to the drawings in which like reference character(s) present corresponding parts throughout:

FIG. 3 is a perspective exemplary illustration of an assembled toilet seat and lid in the open position in accordance with the present invention;

FIG. 4 is a perspective exemplary illustration of an assembled toilet seat and lid in the closed position in accordance with the present invention;

FIG. 5 is a perspective exemplary view of a locking clip and grip in accordance with the present invention;

Figure 1:
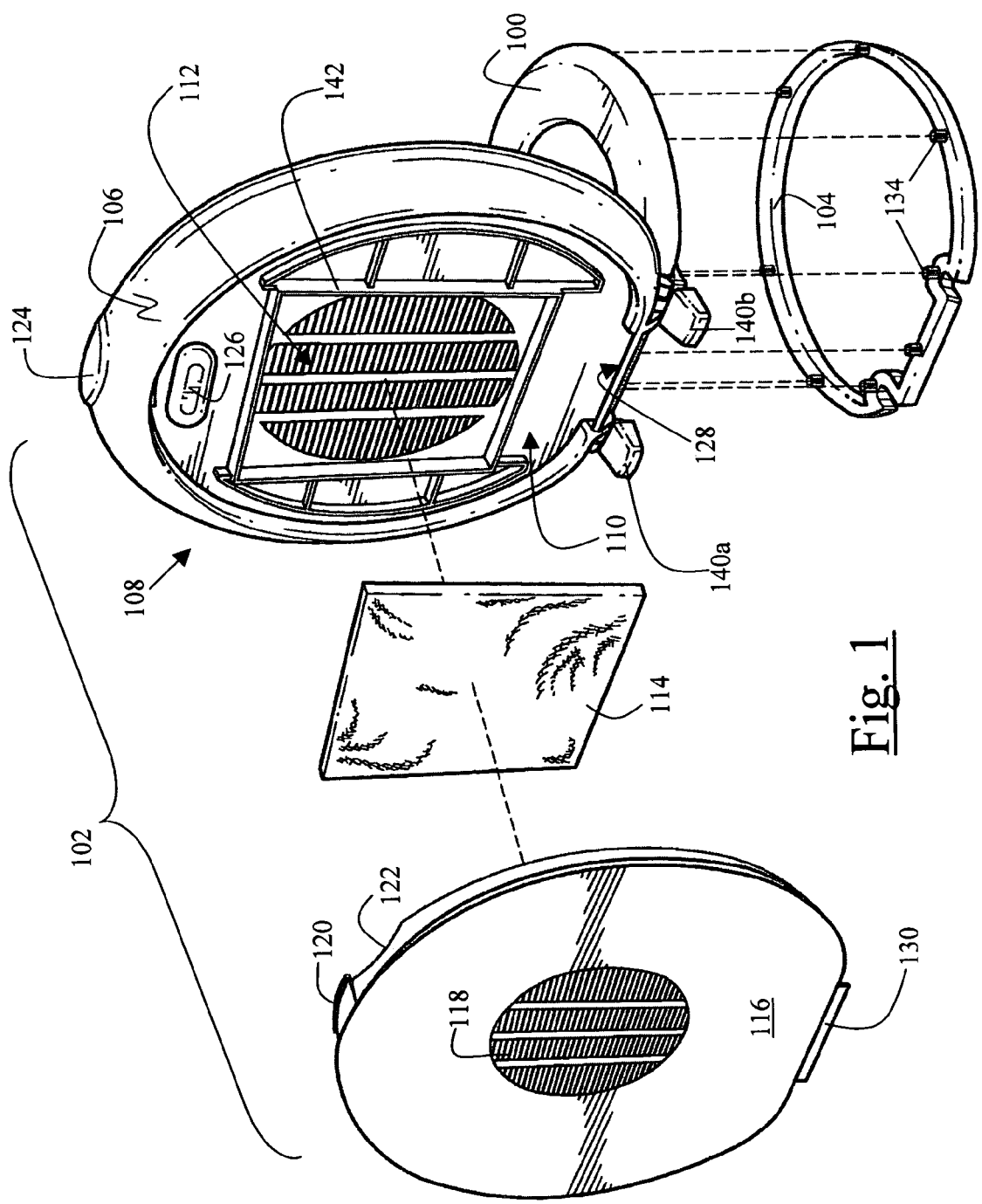
FIG. 1 illustrates a general preferred exemplary toilet seat and lid combination in accordance with the present invention.

DETAILED DESCRIPTION OF THE INVENTION (1) Introduction

Most conventional toilet lids or seats use complicated mechanical contraptions to vacuum out odors or germs from toilet bowls from the sides of the toilet seats or bowls. The toilet seats or bowls are equipped with side-vents on the circumference or periphery of bowls or seats that are connected to an electrical fan with a vent pipe that connects to an air duct with another electrical exhaust fan for removal of odors and germs from the building. Although the act of flushing spews out most of the fecal and urinary droplets from the toilet bowl (the "sneeze effect") vertically upward, the mechanical devices vacuum the odor and germs horizontally through the sides of the toilet.

The present invention provides a non-mechanical toilet seat and lid combination for detection, collection, containment, neutralization, and elimination of aerosolized contaminants, fecal and urinary matter, and various airborne toxins, viral, and bacterial mist, and works with the natural fluid dynamics caused by flushing a toilet that generates the vertical ascension of aerosols. During every flush cycle, a vertically ascending aerosol (spray) is created when the water is pushed in the bowl, and a suction is created within the bowl when the water leaves the bowl, pulling the air into the bowl. The present invention can be used to detect, collect, contain, and sanitize most of the aerosolized contaminants, fecal and urinary matter, and various airborne toxins, viral, and bacterial mist as a result of the vertical ascension of aerosols after every flush, and closes the gaps between the toilet lid and seat, and seals the toilet seat and bowl for any possible horizontal travel of the aerosol caused by flushing.

Before providing details regarding the various aspects of the invention, first an overview of the present invention is provided, which describes the interconnections and operation of various major components in order to provide a more tangible understanding thereof without getting lost in the details. Next, an explicatory section is provided in which the various major components presented in the overview are described in detail.

(2) Overview

The present invention provides a device comprising a lid that fully covers edges of a container such as a toilet bowl for containment of exiting aerosolized contaminants. The lid includes housing for accommodating an article, the nonlimiting examples of which may include any one or combination of well-known sensors, analyzers, collectors, filters, sanitizers, etc. The housing includes a top vent aligned along atop of a bottom vent, with the top vent optionally smaller in size than the bottom vent, with the housing, the top vent, and the bottom vent located normal to a natural vertical upward move of the aerosolized contaminants due to the force of the flush. When the lid of the present invention is in the closed position, the lid and the article within the lid housing can be used to detect, collect, contain, neutralize, and eliminate contaminants that ascend through the top of the container, without the use of any moving parts. In case of a toilet bowl, the contaminants are aerosolized and spewed vertically upward by the normal action of flushing. Hence, the present invention uses the natural fluid dynamics caused by flushing a toilet (and not mechanical systems) to detect, collect, contain, neutralize, and eliminate most of the aerosolized contaminants, fecal and urinary matter, and various airborne toxins, viral, and bacterial mist as a result of the vertical ascension of aerosols or vapors.

(3) Explication

The following paragraphs describe in detail the various embodiments of the present invention, with the preferred embodiment illustrated in FIGS. 1 to 10. Referring to FIGS. 1 to 10 and, FIG. 1 in particular, the lid 102 of the present invention is comprised of a main lid section 108 having a shroud 106 that fully covers a gap between the lid 102 and a seat 100 by extending past a bottom edge of the toilet seat 100. When the lid 102 is in a fully closed position (illustrated in FIG. 4), the shroud 106 blocks exiting of fecal and urinary aerosols during the act of flushing. The proximal end of the shroud 106 includes a lid lift tab 124 that facilitates in raising and lowering the lid 102 without touching the seat 100. As illustrated, the lid lift tab 124 is arched, and extends out, past the outer edge of the seat 100 to allow a person to use a finger to lift or lower the lid 102.

Figure 2:
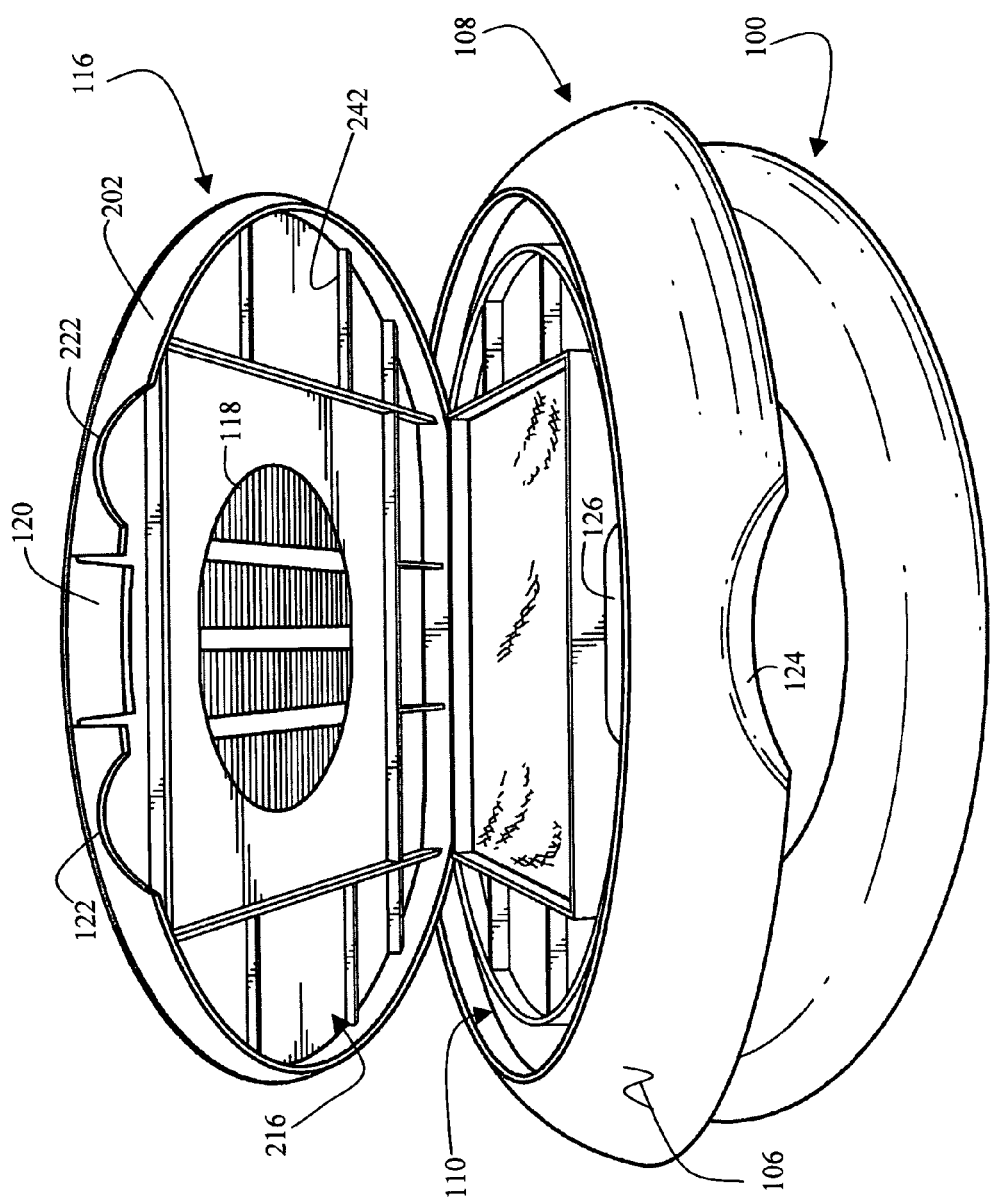
FIG. 2 is a perspective exemplary front illustration of a the toilet seat, lid, and lid cap, unassembled, in accordance with the present invention.

As further illustrated in FIG. 1, the main lid section 108 includes a housing 110 comprised of a vent or air holes 112. The housing 110 can be used to store any article 114 of appropriate size, the nonlimiting examples of which may include one or any combination of well-known sensors, analyzers, filters, collectors, sanitizers, etc. to detect, collect, contain, neutralize, and or eliminate aerosolized contaminants that ascend vertically out of the toilet bowl as a result of flushing, without any moving parts, when the lid 102 is in the closed position. The housing 110 also includes structures 142 for securing the article 114, and for providing structural integrity and strength for the lid 102. The housing 110 further includes an elongated recessed portion 128 at a distal end near the two coupling hinges 140a and 140b for accommodating a protruded tab 130 located at a distal end of a lid cap 116. The coupling hinges 140a and 140b reference a mechanism that couples the entire lid/seat combination to the toilet bowl. In addition, the housing 110 includes an opening 500 at a proximal end thereof (best illustrated in FIG. 5) for receiving a locking clip 120 located at a proximal end of the lid cap 116. As best illustrated in FIGS. 1, 2, and 5, the locking clip 120 is comprised of a cut-section from the circumference edge 202 of the lid cap 116, suspended in a cantilever manner that interlocks within the edges of opening 500 of the housing 110.

The housing 110 is closed by a removable lid cap 116, which also includes a vent or air holes 118 at a location commensurate with a location of the vent or air holes 112 on the main lid section 108. In general, it is preferred (optionally, only) if the size of the vent 118 on the lid cap is made smaller than the size of the vent 112 on the main lid section 108. However, the device of the present invention can function without size differences between the vents. In general, the size difference (smaller top vent and larger bottom vent) accelerates the venting process. That is, this difference may facilitate the acceleration of the vertical ascension of aerosols through the vent 112, the housing 110, pushing air out of the vent 118. As best illustrated in FIGS. 1 and 2, the lid cap 116 includes a right 222 and a left 122 arch located at a proximal end thereof, near both sides of the locking clip 120 for facilitating the removal and insertion of the lid cap 116 from the main lid section 108. As best illustrated in FIGS. 2 and 4, the circumference edge 202 of the lid cap 116 is fully inserted inside the housing 110. The underside 216 of the lid cap 116 also includes support structure 242 for added strength.

Figure 6:
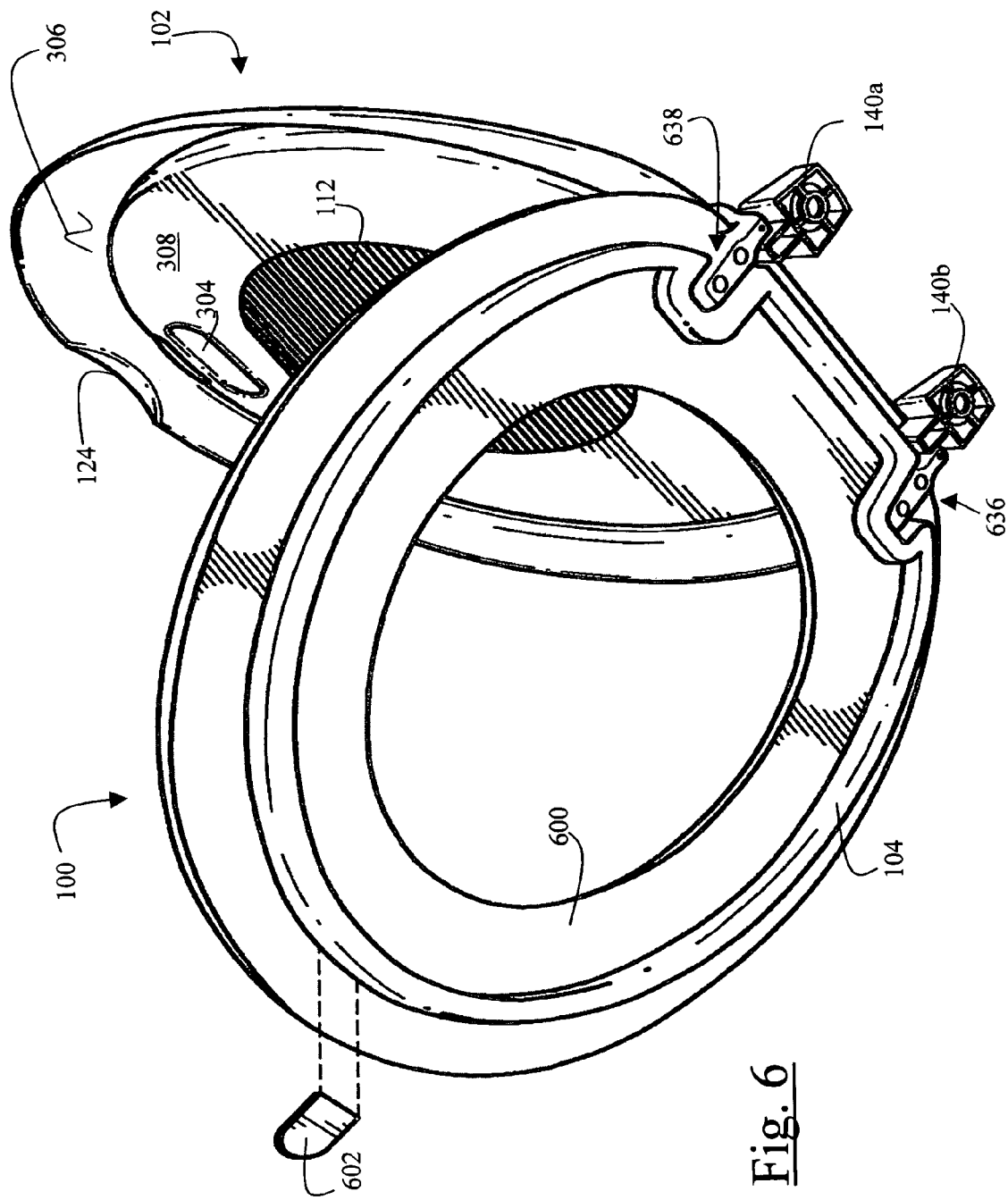
FIG. 6 is a perspective exemplary illustration of the underside of the toilet seat in accordance with the present invention.
Figure 7:
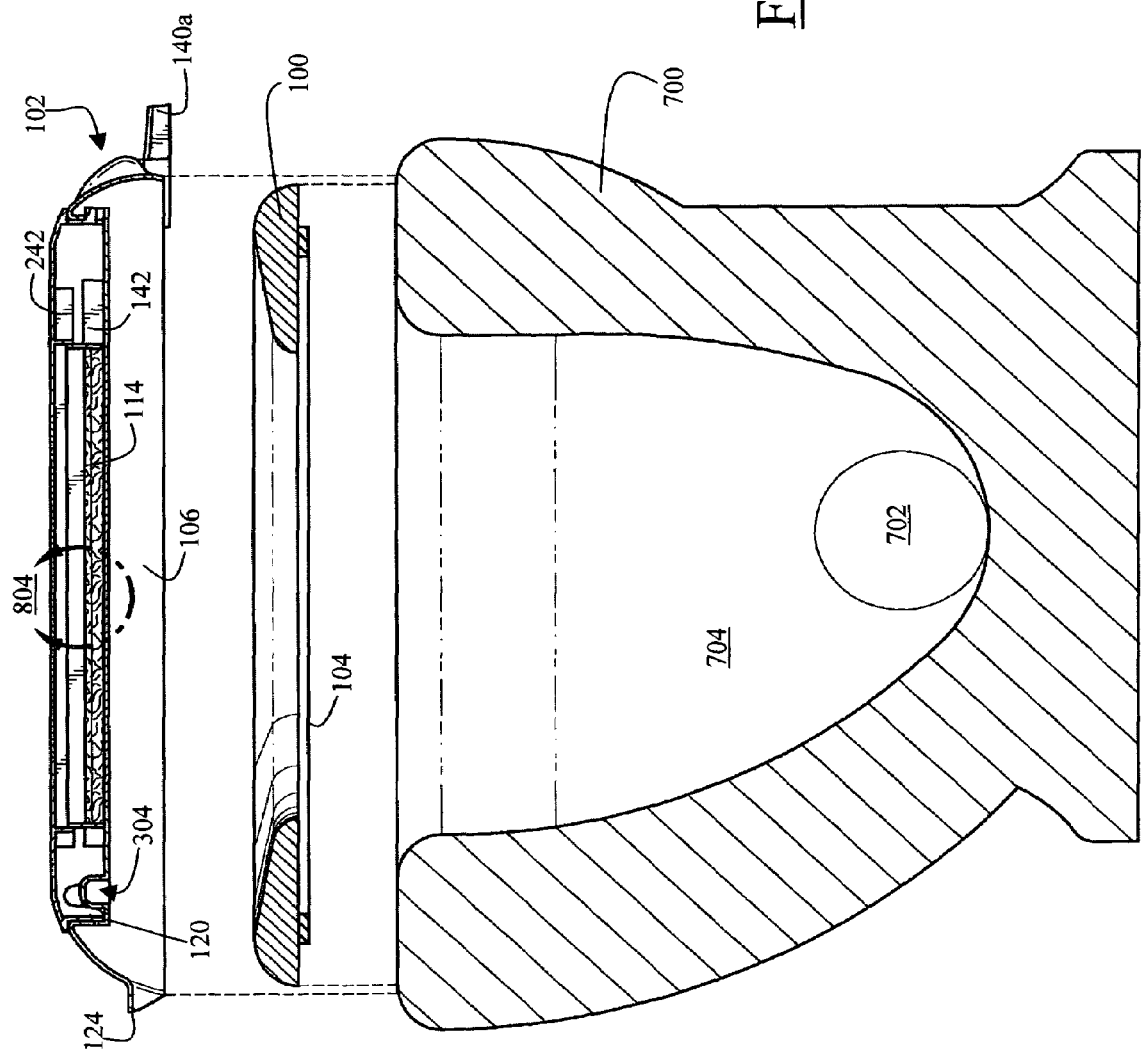
FIG. 7 is a side cross-sectional view, illustrating an exemplary toilet bowl seat, and lid in accordance with the present invention.

Referring to FIGS. 1, 6, and 7, the seat 100 is comprised of a seal 104 that is connected to the underside 600 of the seat 100 by one or more seal installation tabs 134 to enclose the gap between the toilet seat 100 and a top surface opening of the toilet bowl 700 (FIG. 7). This closing of the gap prevents the exiting of any possible horizontally moving toxins, fecal, or other contaminant aerosols due to flushing when the lid and seat are in the closed position (illustrated in FIG. 4). The seal installation tabs 134 are inserted into a commensurate number of apertures (not shown) within the underside 600 of the seat 100. As best illustrated in FIG. 6, the seal 104 is continuously placed around the underside 600 of the toilet seat 100, veering around connection mechanisms 636 and 638 at a distal end of the toilet seat 100, near the coupling hinges 140a and 140b. The connection mechanisms 636 and 638 may be used to couple the seat 100 to the lid 102. As further illustrated in FIG. 6, the toilet seat 100 and lid 102 combination of the present invention also includes an optional seat lift tab 602 that facilitates in raising and lowering of the toilet seat 100.

FIG. 3 is a perspective exemplary illustration of an assembled toilet seat 100 and lid 102 in the open position in accordance with the present invention, which shows the underside 308 of the main lid section 108 of lid 102. As illustrated, approximately at the middle section of the underside 308 is the underside of the vent 112. The underside 308 further includes a cavity 304 at a proximal end near the opening 500 (best illustrated in FIG. 5) for insertion of fingers for grasping the lid cap for facilitating the removal of the locking clip 120 from the opening 500. The opposite side of the cavity 304 is referred to by the reference number 126 in the FIGS. 1 and 2, and is illustrated as a bump or protuberance. FIG. 3 also illustrates the underside 306 of the shroud 106.

FIG. 4 is a perspective exemplary illustration of the assembled toilet seat 100 and lid 102 combination in the closed position in accordance with the present invention. As illustrated, the lid 102 completely covers the seat 100 by the shroud 106, and further, as illustrated in both FIGS. 3 and 4, unlike the prior art contraptions, the seat 100 and lid 102 combination of the present invention maintain the same esthetic look and feel of a conventional toilet seat and lid. In particular, the circumference edge 202 of the lid cap 116 fully inserts into the housing 110, enabling a top surface of the lid cap 116 to be flush with the main lid section 108.

Figure 8:
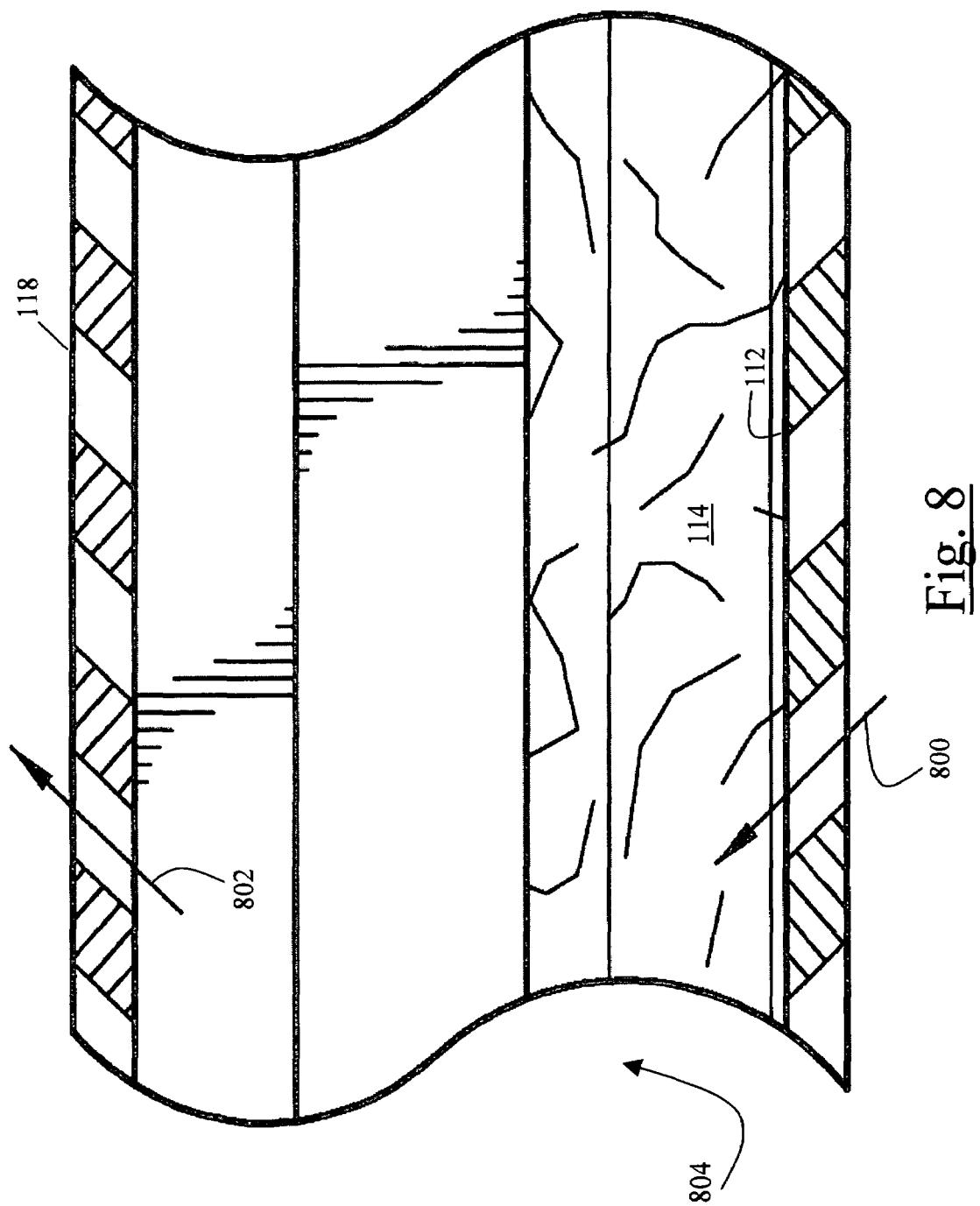
FIG. 8 is an exploded cross-sectional view of an exemplary vent in accordance with the present invention.

FIGS. 7 to 10 illustrate the toilet seat 100 and lid 102 combination of the present invention in relation to the toilet bowl 700. FIG. 7 is a side cross-sectional view, illustrating the cooperative relationship and arrangement of the toilet seat 100, the lid 102, and the toilet bowl 700. The figure also illustrates the toilet water 704 within the bowl 700 and a drainpipe 702. The broken circular arrows 804 in FIG. 7 refer to the drawing illustrated in FIG. 8, which is an enlarged cross-sectional view of the exemplary lid 102 of the present invention, including the article 114 housed within the housing 110. As best illustrated in FIG. 8, during the act of flushing, aerosolized contaminants 800 are spewed vertically up, towards the lid 102, passing through the vent 112 and the article 114 (e.g., a known filter), with clean air 802 coming out of the vent 118 of the lid cap 116.

Figure 9:
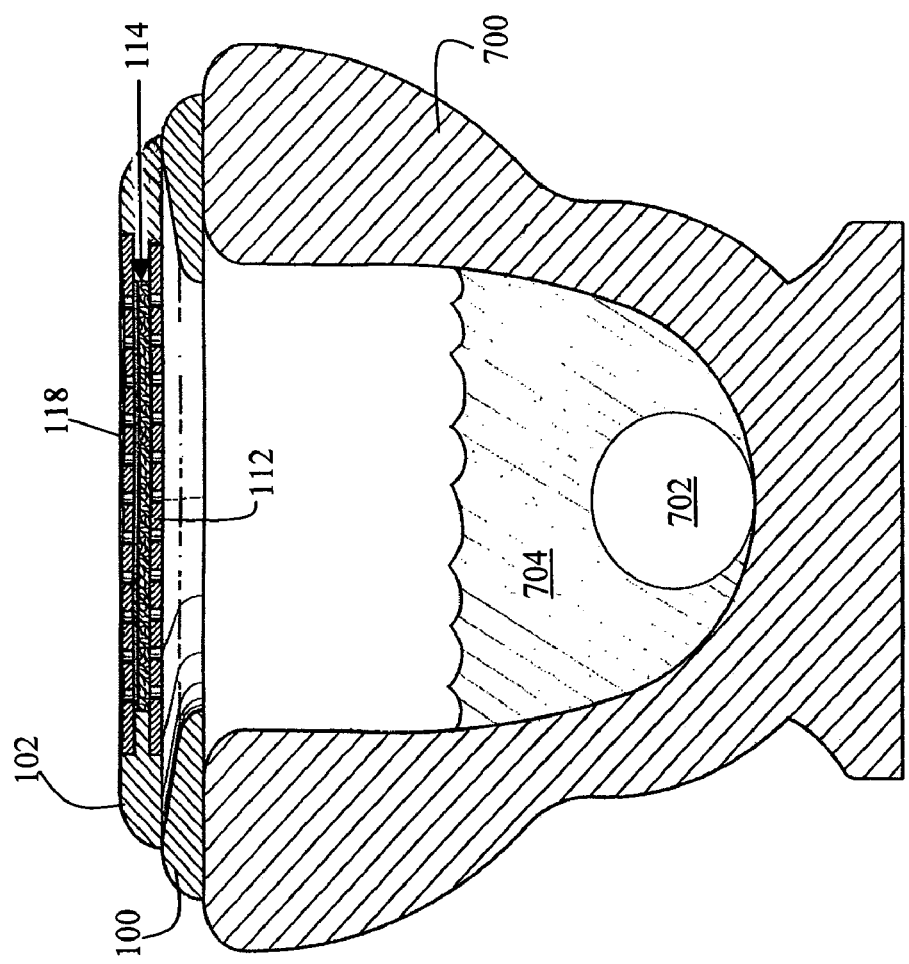
FIG. 9 is a front cross-sectional view, illustrating an exemplary toilet bowl, seat, and lid in accordance with the present invention.
Figure 10:
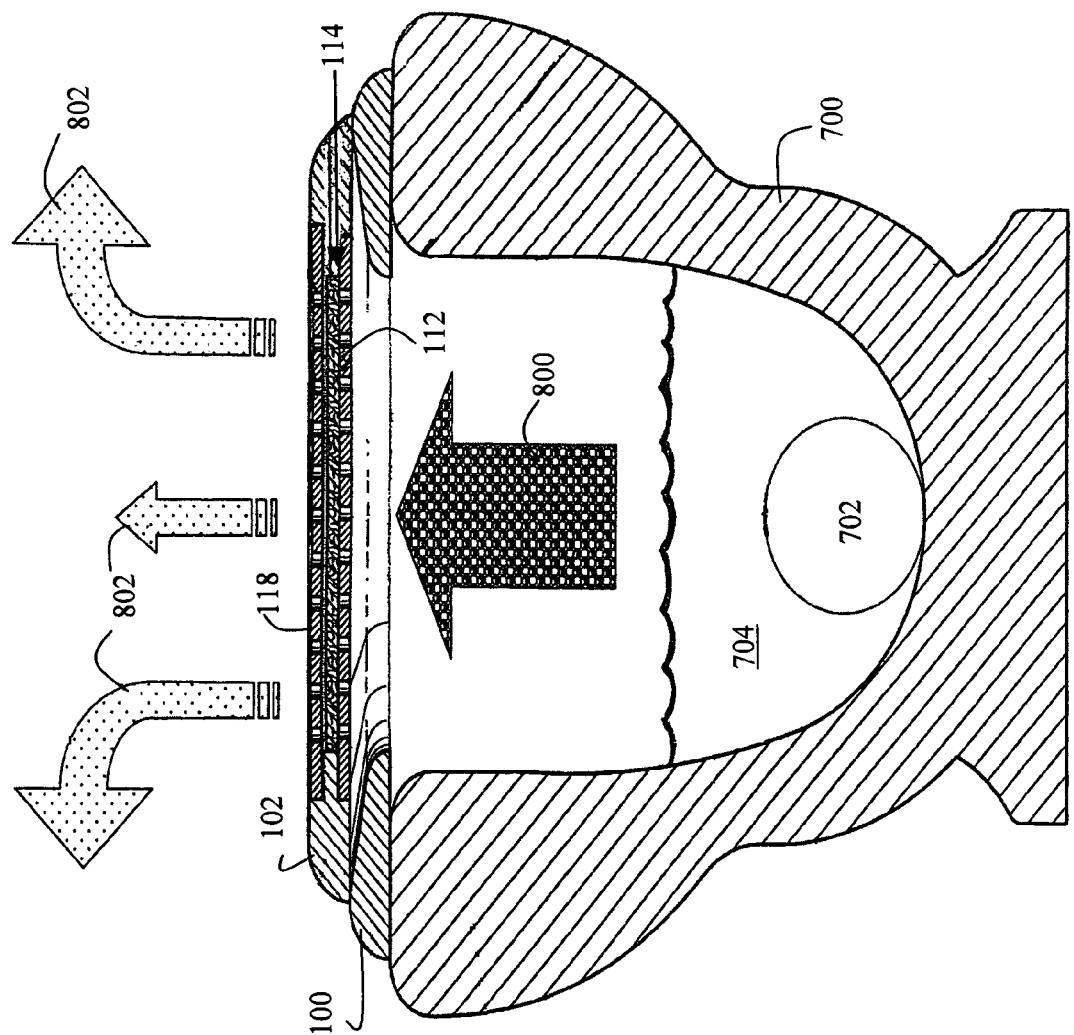
FIG. 10 is a front cross-sectional view, illustrating an exemplary toilet bowl, seat, and lid during flushing action, including the flow dynamics of aerosolized contaminants in accordance with the present invention.

FIG. 9 illustrates a front cross-sectional view, showing a fully assembled and connected toilet bowl 700, seat 100, and lid 102, and FIG. 10 is the same view, illustrating the flushing action, including the flow dynamics of aerosolized contaminants 800 in accordance with the present invention. In both FIGS. 9 and 10, the shroud 106 is not illustrated for better clarity. When the seat 100 and the lid 102 are in the closed position, during the first half of the flush cycle (illustrated in FIG. 10), a vertically ascending toxic, bacterial, and viral aerosol (spray) 800 is created (the "sneeze effect") when the toilet water 704 is pushed in the bowl 700. The aerosol or other contaminants (toxins, bacteria, viruses, etc.) 800 is mostly spewed vertically, and is forced to exit through the vent or air holes 112 and the housing 110, but only uncontaminated air 802 is exited through the vent or air holes 118. Upon coming into contact with the article 114 within the housing 110 (which may contain any combination of sensors, analyzers, container dishes, filter-sanitizers, etc.), most of the contaminants or bacteria and viruses are detected, collected, contained and or killed by the article 114, allowing uncontaminated air 802 to exit from the vent 118. During second half of every flush cycle, a suction is created within the bowl 700 when the toilet water 704 leaves the bowl 700 through the drainpipe 702, pulling the air into the bowl 700 through the vent or air holes 118, the housing 110, and the vent or air holes 112. Accordingly, the present invention prevents droplets or airborne toxins, contaminants, or other bacterial or viral aerosols 800 to plume and permeate out of the toilet bowl 700 when the seat 100 and lid 102 combination of the present invention are in the closed position.

Figure 11:
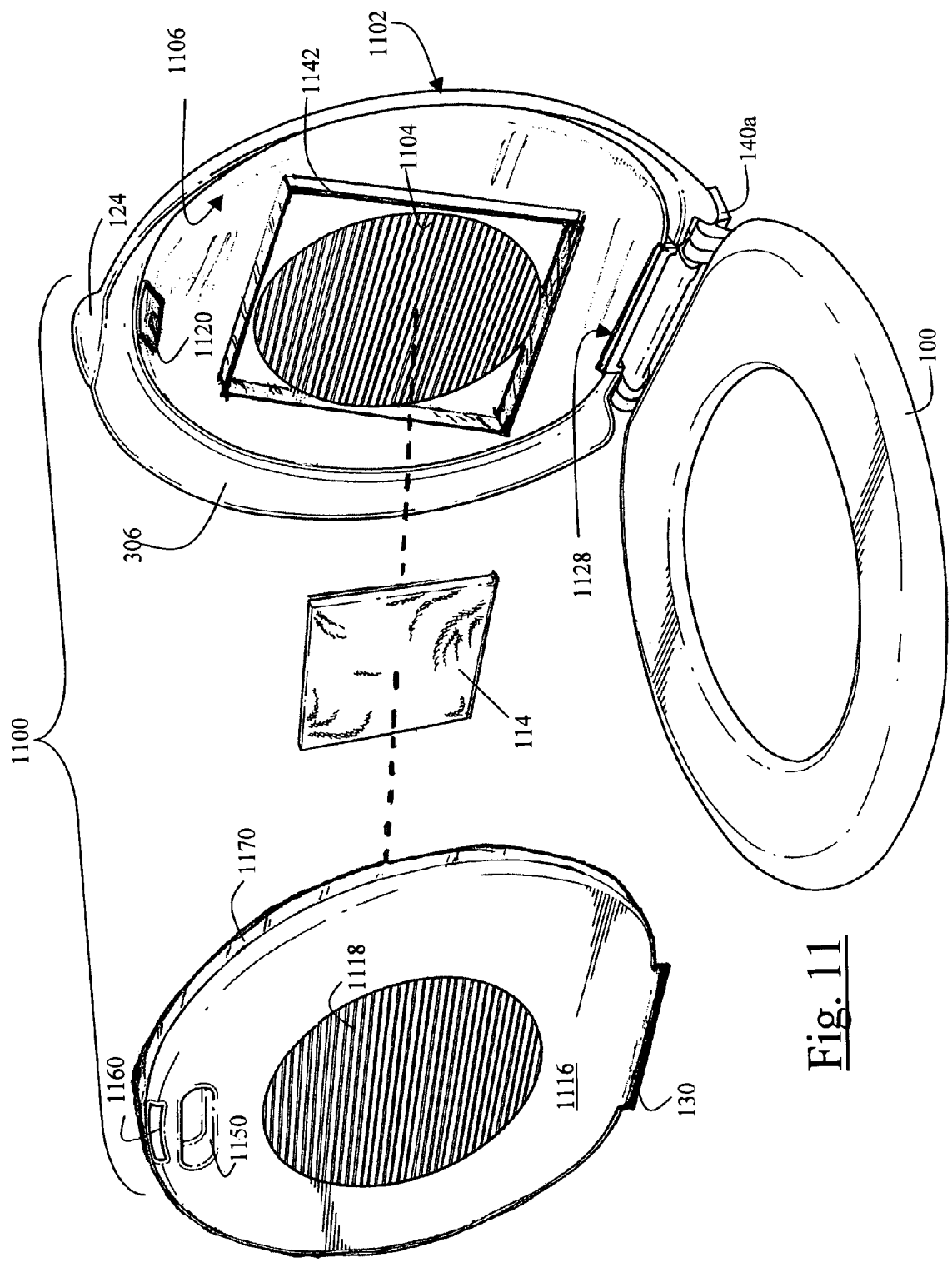
FIG. 11 is an alternative embodiment, illustrating an exemplary toilet seat and lid in accordance with the present invention.

FIG. 11 is an alternative embodiment, illustrating an exemplary toilet seat 100 and lid 1100 in accordance with the present invention in which the lid cap 1116 couples to the underside housing 1106 of the main lid section 1102, combining to form the lid 1100. As FIG. 11 illustrates, the main lid section 1102 of the lid 1100 includes the housing 1106, which is comprised of a vent or air holes 1104. The housing 1106 can be used to store any article 114 of appropriate size to detect, collect, contain, neutralize, and eliminate aerosolized contaminants 800 that ascend vertically out of the toilet bowl 700 as a result of flushing, without any moving parts, when the seat and the lid are in the closed position. The housing 1106 also includes structures 1142 for securing the article 114, and for providing structural integrity and strength for the lid 1100. The housing 1106 further includes an elongated recessed portion 1128 at a distal end near the two coupling hinges 140a and 140b for accommodating a protruded tab 130 located at the distal end of a lid cap 1116. The housing 1106 further includes a locking clip 1120 located at a proximal end of the housing 1106, projected outward from the underside of the main lid section 1102 of the lid 1100, and is received by an opening 1160 at a proximal end of the lid cap 1116. The protruded tab 130 is inserted within the elongated recess 1128 of the housing 1106, and the locking clip 1120 of the housing 1106 is snapped into the opening 1160 of the lid cap 1116 for securing the lid cap 1116 onto the main lid section 1102 for enclosing the housing 1106.

Figure 12:
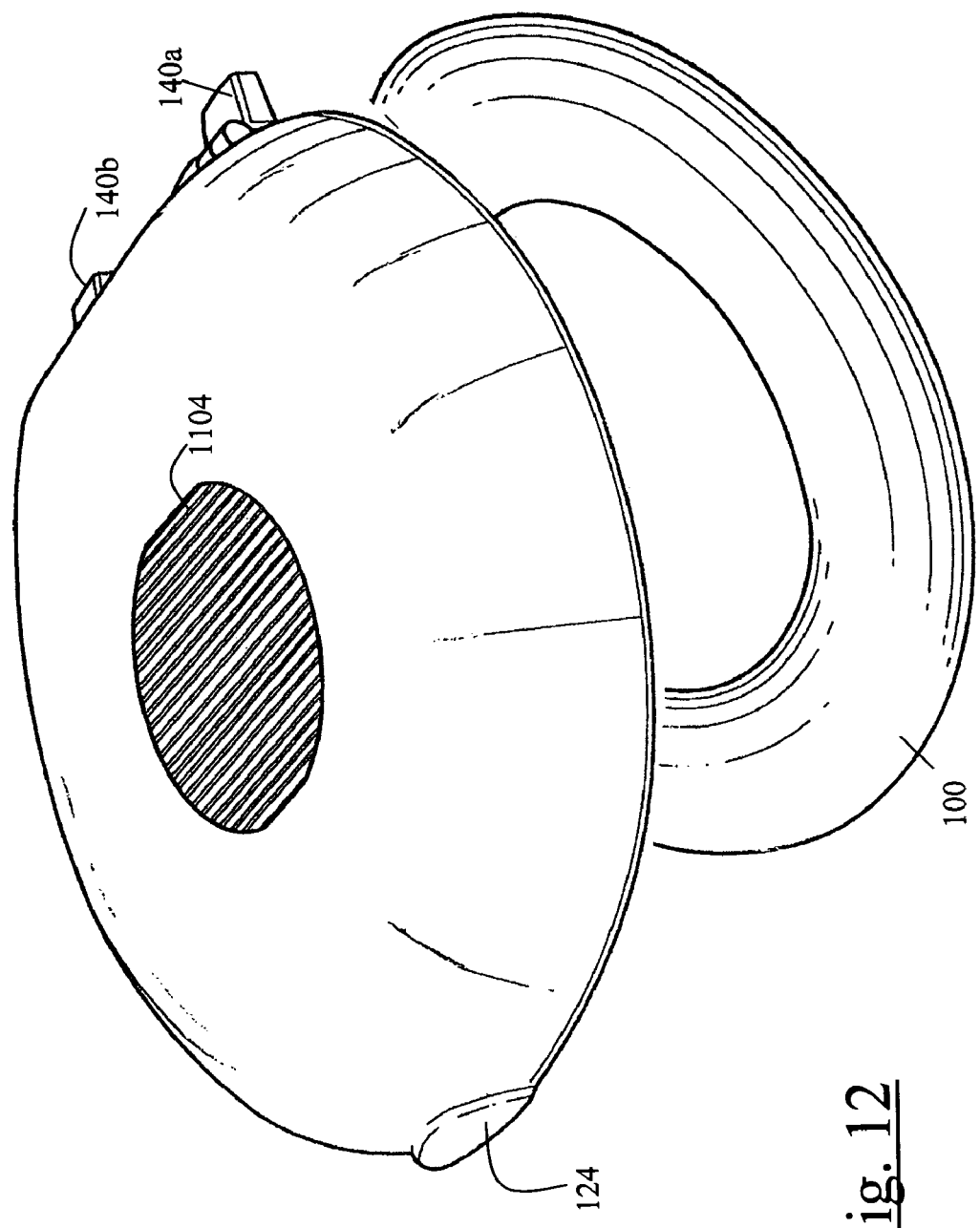
FIG. 12 is an exemplary perspective view, illustrating the assembled toilet seat and lid of FIG. 11 in accordance with the present invention.

The housing 1106 is closed by the removable toilet lid cap 1116, which also includes a vent or air holes 1118 at a location commensurate with a location of the vent or air holes 1104 on the main lid section 1102. In general, it is preferred (optionally, only) if the size of the vent 1118 on the lid cap 1116 is made larger than the size of the vent 1104 on the main lid section 1102. However, the device of the present invention can function without size differences between the vents. In general, the size difference (smaller top vent and larger bottom vent) accelerates the venting process. That is, this difference may facilitate the acceleration of the vertical ascension of aerosols through the vent 1118, the housing 1106, pushing air out of the vent 1104. The circumference edge 1170 of the lid cap 1116 is fully inserted inside the main lid section 1102. A cavity 1150 at a proximal end near the opening 1160 is used for insertion of fingers for grasping the lid cap for facilitating the removal of the locking clip 1120 from the opening 1160. The underside of the lid cap 1116 (not shown) also includes support structure for added strength. The remaining components are identical to the preferred embodiment illustrated in FIGS. 1-10. FIG. 12 illustrates the topside of the lid 1100, including the topside of the vent 1104.

Figure 13:
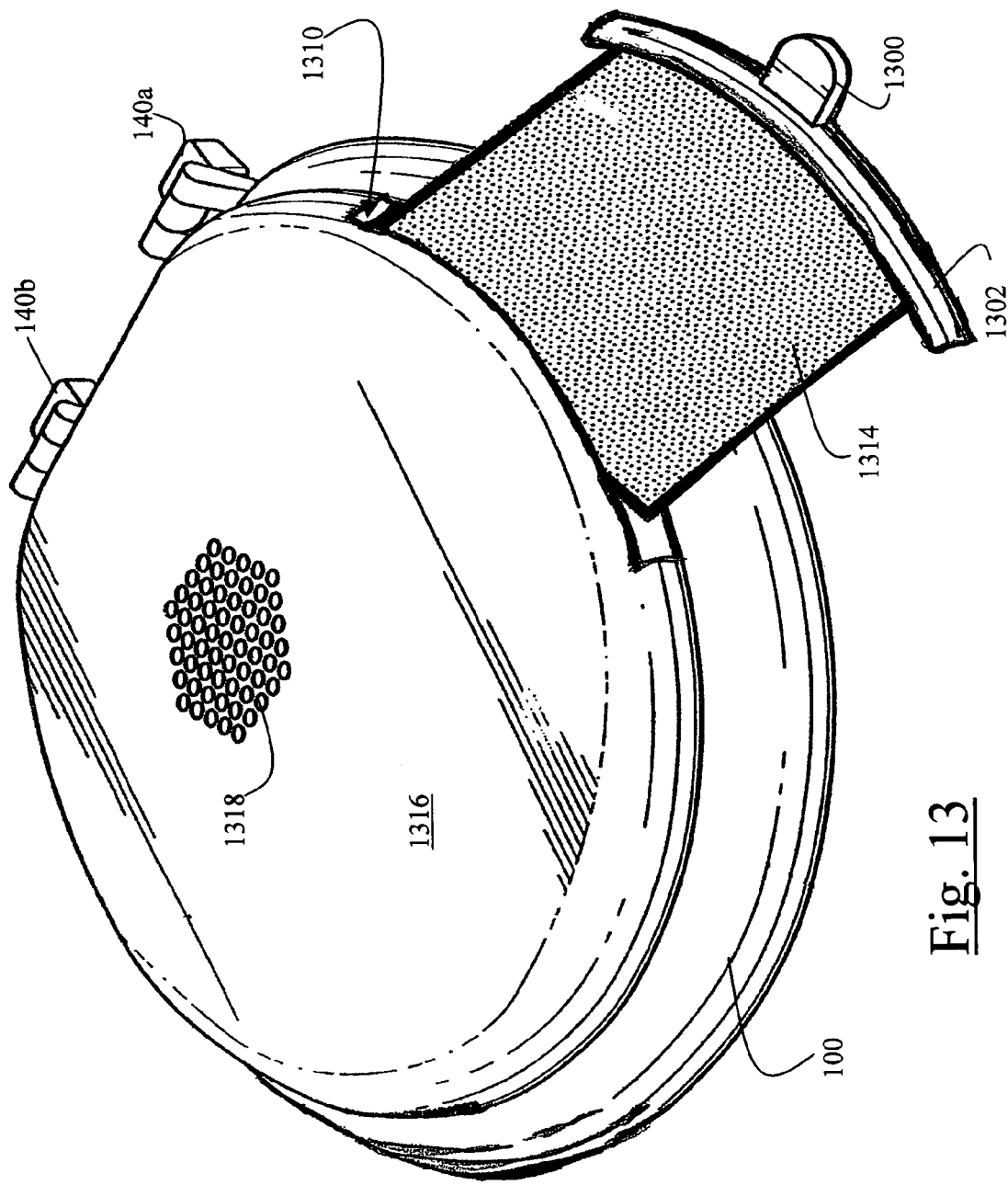
FIG. 13 is another alternative embodiment, illustrating an exemplary toilet seat and lid in accordance with the present invention.
Figure 14:
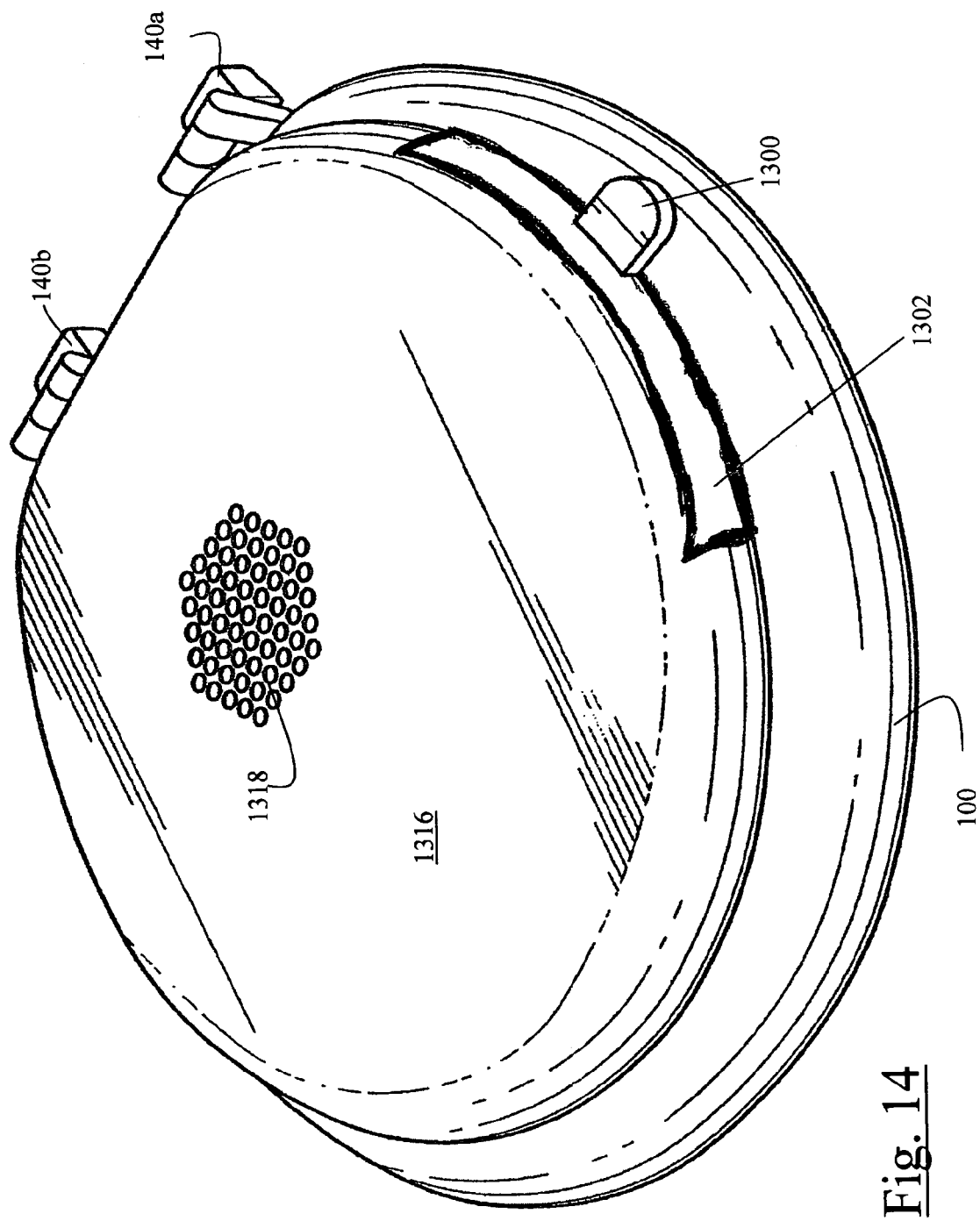
FIG. 14 is an exemplary illustration of the toilet seat and lid shown in FIG. 13, in a closed position in accordance with the present invention.
Figure 15:
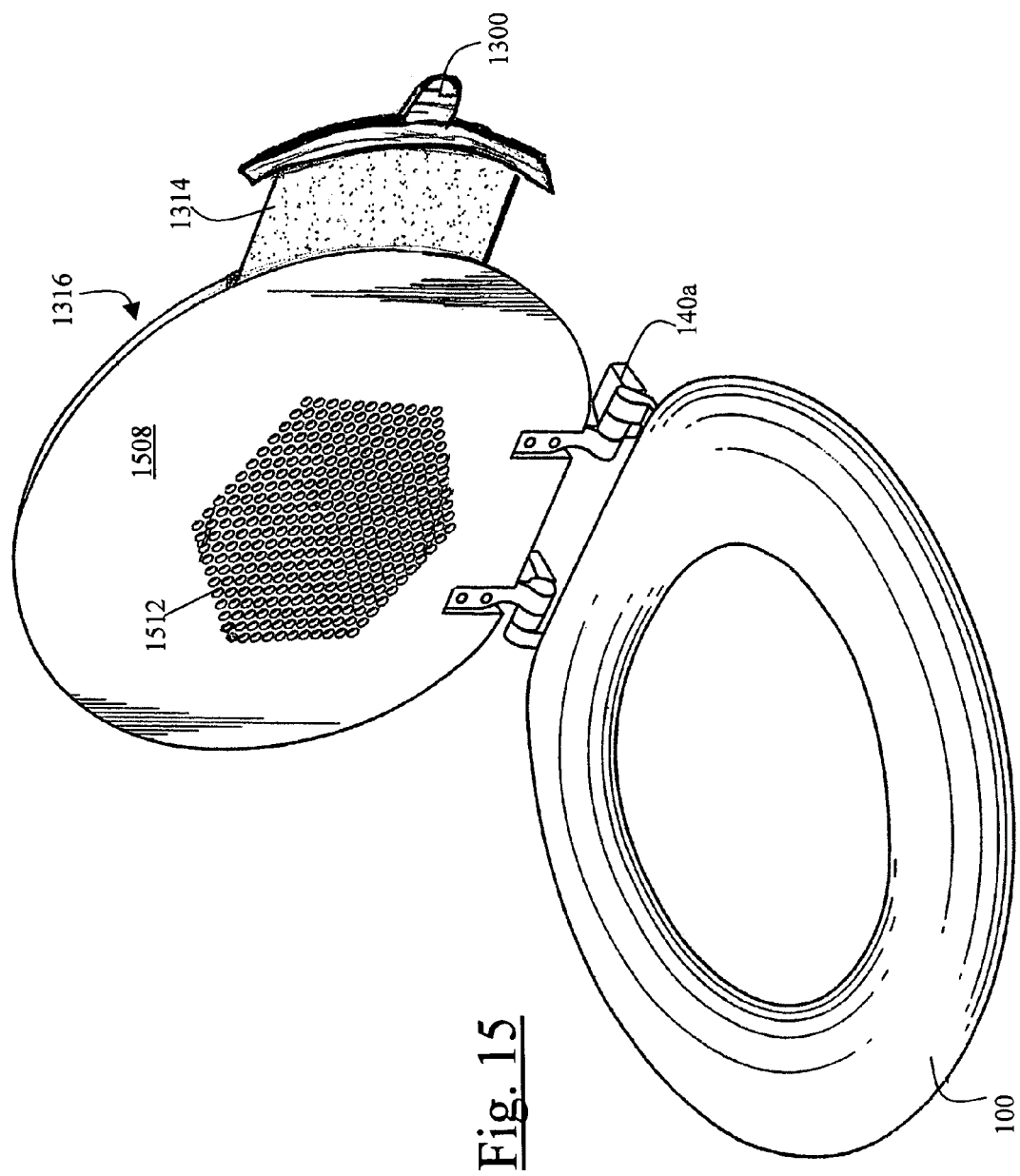
FIG. 15 is an exemplary illustration of the toilet seat and lid shown in FIG. 13, in an open position in accordance with the present invention.

FIG. 13 is another alternative embodiment, illustrating an exemplary toilet seat 100 and lid 1316 in accordance with the present invention. As illustrated, the lid 1316 is comprised of vent or air holes 1318, and includes housing 1310 for insertion of an article 1314 therein, the nonlimiting examples of which may include one or any combination of sensors, analyzers, filters, collectors, sanitizers, etc. In this embodiment, the article 1314 further includes a tab handle 1300, and a coupler 1302, which connects the tab handle 1300 to the article 1314. FIG. 14 is an exemplary illustration of the toilet seat 100 and lid 1316 combination shown in FIG. 13, with the article 1314 fully inserted inside the housing 1310. FIG. 15 is an exemplary illustration of the same toilet seat 100 and lid 1316 combination shown in FIG. 13, but with the lid 1316 in an open position, and the article 1314 moved out of the housing 1310 to an extended position. As illustrated, the underside 1508 of lid 1316 is also comprised of vent or air holes 1512, with vent 1318 optionally configured smaller in size than the underside vent 1512.

Although the invention has been described in considerable detail in language specific to structural features and or methodological steps, it is to be understood that the invention defined in the appended claims is not necessarily limited to the specific features or steps described. Rather, the specific features and steps are disclosed as preferred forms of implementing the claimed invention. Therefore, while illustrative embodiments of the invention have been described, numerous variations and alternative embodiments will occur to those skilled in the art. For example, the protruded tab of the lid cap and the elongated recess on the main lid section for any of the embodiments may be replaced by a hinge mechanism to allow the opening and closing of the lid cap in relation to the main lid section in the same manner as the lid is opened and closed in relation to the seat. This would allow the lid cap to open and close from the top, and pivot on the hinge at the bottom, which connects to the main lid section. Another alternative would be to place the same hinge mechanism at the proximal end (the top of the main lid section and the lid cap) to replace the locking clip and aperture combination instead, and provide well-known locking schemes at a distal end, replacing the protruded tab of the lid cap and the elongated recess on the main lid section. This would allow the lid cap to open and close from the bottom, and pivot on the hinge at the top, which connects to the main lid section. Such variations and alternate embodiments are contemplated, and can be made without departing from the spirit and scope of the invention.

What is claimed is:

1. A device for detection, collection, containment, neutralization, and elimination of aerosolized contaminants, comprising:
    a toilet lid coupled with a toil seat, and when the toilet lid is in a closed position, an entire underside of the toilet lid directly and physically contacts and rests on a top surface of the toilet seat;
    the toilet lid further including a shroud section that fully covers and extends past an exterior facing edge of the toilet seat and a top surface opening of a toilet bowl when the toilet lid is in the closed position, with the shroud directly and physically contacting an entire exterior facing edge of the toilet seat;
    the underside of the toilet lid and the shroud fully enclose a first gap between the toilet lid and the toilet seat when the toilet lid is in the closed position, containing exiting aerosolized contaminants and blocking exiting of aerosolized contaminants through the first gap during a flush;
    the toilet seat is further comprised of a continuous seal coupled with an underside of the toilet seat to fully enclose a second gap between the toilet seat and the top surface opening of the toilet bowl when the toilet seat is in the closed position, containing exiting aerosolized contaminants and blocking exiting of aerosolized contaminants through the second gap during the flush;
    the toilet lid further having a housing for accommodating an article;
    the housing comprising a top vent and a bottom vent;
    with the toilet lid and the toilet seat in closed positions to close the first and the second gaps, when water is delivered into the toilet bowl, the delivered water displaces and compresses air within the toilet bowl, generating an increasing air pressure therein that is pushed upward as a volume of delivered water continues to increase and fill the toilet bowl, with the increased volume of water pushing the pressurized air and the aerosolized contaminants within the toilet bowl vertically up to ascend and exit the toilet bowl through the bottom vent and then out the top vent, while the closed first and the second gaps block exiting of the aerosolized contaminants;
    with the aerosolized contaminants detected, collected, contained, neutralized, and eliminated by the article within the housing, allowing only uncontaminated air out of the top vent, and only through a natural upward movement of the aerosolized contaminants due to the flush cycle, without using electrical or moving components.

2. The device of claim 1, further including a lid cap having one of the top vent and the bottom vent.

3. The device as set forth in claim 2, wherein the housing further comprises:
    an elongated recessed section at a distal end of the housing for accommodating a protruded tab located at a distal end of the lid cap; and
    an opening at a proximal end of the housing for accommodating a locking clip located at a proximal end of the lid cap;
    whereby the protruded tab of the lid cap is inserted within the elongated recess of the housing, and the locking clip of the lid cap is snapped into the opening of the housing for securing the lid cap onto the housing.

4. The device as set forth in claim 2, wherein the housing further comprises:
an elongated recessed section at a distal end of the housing for accommodating a protruded tab located at a distal end of the lid cap; and
an opening at a proximal end of the lid cap for accommodating a locking clip located at a proximal end of the housing;
whereby the protruded tab of the lid cap is inserted within the elongated recess of the housing, and the locking clip of the housing is snapped into the opening of the lid cap for securing the lid cap onto the housing.

5. The device as set forth in claim 3, wherein the lid cap further includes a right arch and a left arch located at a proximal end of the lid cap, proximal to either side of the locking clip for facilitating the removal and insertion of the lid cap from the housing.

6. The device as set forth in claim 4, wherein the lid cap further includes a right arch and a left arch located at a proximal end of the lid cap, proximal to either side of the opening for facilitating the removal and insertion of the lid cap from the housing.

7. The device as set forth in claim 2, wherein the circumference edges of the lid cap fully inserts into the housing.

8. The device as set forth in claim 1, wherein the housing includes structure for securing the article therein, and for providing structural integrity and strength for the lid.

9. The device as set forth in claim 1, wherein the proximal end of an upper shroud section includes a lid lift tab for opening and closing of the lid.

10. The device as set forth in claim 3, wherein a proximal end of an underside of the lid, adjacent to the opening is comprised of a cavity for insertion of fingers for grasping the underside of the lid for removal of the locking clip from the opening.

11. The device as set forth in claim 4, wherein a proximal end of a top side of the lid cap, adjacent to the opening is comprised of a cavity for insertion of fingers for grasping the lid cap for removal of the locking clip from the opening.

12. The device as set forth in claim 3, wherein the locking clip is comprised of a cut-section of the circumference edge of the lid cap, suspended in a cantilever manner, with an elongated free side having a protrusion that locks within the opening of the lid.

13. The device as set forth in claim 4, wherein the locking clip is projected out and is integral with an underside of the lid, with an elongated free side having a protrusion that locks within the opening of the lid cap.

14. The device as set forth in claim 1, wherein the article includes a handle that allows for insertion and removal in a sliding manner within the housing.

15. The device as set forth in claim 1, wherein the article is replaceable.

16. The device as set forth in claim 1, wherein the top vent is smaller than the bottom vent.

17. The device as set forth in claim 2, wherein the lid cap couples to a main lid section for forming the lid.

18. A device for detection, collection, containment, neutralization, and elimination of aerosolized contaminants, comprising:
a toilet lid coupled with a toil seat, and when in a closed position, a first gap between the toilet lid and the toilet seat is fully enclosed to contain and block exiting aerosolized contaminants through the first gap during a flush;
the toilet seat is comprised of a continuous seal coupled with an underside of the toilet seat to fully enclose a second gap between the toilet seat and the top surface opening of the toilet bowl when the toilet seat is in the closed position to contain and block exiting aerosolized contaminants through the second gap during the flush;
the toilet lid further having a housing for accommodating an article, with the housing having a first vent and a second vent;
with the toilet lid and the toilet seat in closed positions to close the first and the second gaps, when water is delivered into the toilet bowl, the delivered water displaces and compresses air within the toilet bowl, generating an increasing air pressure therein that is pushed upward as a volume of delivered water continues to increase and fill the toilet bowl, with the increased volume of water pushing the pressurized air and the aerosolized contaminants within the toilet bowl vertically up to ascend and exit the toilet bowl through the bottom vent and then out the top vent, while the closed first and the second gaps block exiting of the aerosolized contaminants;
with the aerosolized contaminants detected, collected, contained, neutralized, and eliminated by the article within the housing, allowing only uncontaminated air out of the top vent, and only through a natural upward movement of the aerosolized contaminants due to the flush cycle, without using electrical or moving components.

19. A method for detection collecting, containing, neutralizing, and eliminating of aerosolized contaminants, comprising acts of:
fully enclosing a first gap between a toilet lid and a toil seat when the toilet lid is moved to a closed position;
fully enclosing a second gap between the toilet seat and a top surface opening of the toilet bowl when the toilet seat is moved to the closed position; and
providing vents to allow for natural vertical upward movement of aerosolized contaminants through the vents during a flush, as a result of the water being pushed into a toilet bowl;
with aerosolized contaminants detected, collected, contained, neutralized, and eliminated by an article within the toilet lid, allowing only uncontaminated air out of the vent, and only through the natural upward movement of the aerosolized contaminants due to the flush cycle, without using electrical or moving components.

* * * * *